(12) United States Patent
Cao

(10) Patent No.: US 8,967,883 B2
(45) Date of Patent: Mar. 3, 2015

(54) MODULAR SURGICAL LASER SYSTEMS

(71) Applicant: CAO Group, Inc., West Jordan, UT (US)

(72) Inventor: Densen Cao, Sandy, UT (US)

(73) Assignee: CAO Group, Inc., West Jordan, UT (US)

( * ) Notice: Subject to any disclaimer, the term of this patent is extended or adjusted under 35 U.S.C. 154(b) by 215 days.

(21) Appl. No.: 13/682,724

(22) Filed: Nov. 20, 2012

(65) Prior Publication Data

US 2013/0103122 A1    Apr. 25, 2013

Related U.S. Application Data

(63) Continuation of application No. 12/035,427, filed on Feb. 21, 2008, now Pat. No. 8,337,097, which is a continuation-in-part of application No. 10/947,055, filed on Sep. 22, 2004, now Pat. No. 7,485,116.

(60) Provisional application No. 60/891,037, filed on Feb. 21, 2007.

(51) Int. Cl.
| | |
|---|---|
| G02B 6/36 | (2006.01) |
| A61N 5/06 | (2006.01) |
| A61B 18/22 | (2006.01) |
| A61B 18/18 | (2006.01) |
| A61B 17/00 | (2006.01) |
| A61B 18/20 | (2006.01) |
| A61N 5/067 | (2006.01) |

(52) U.S. Cl.
CPC . *A61N 5/06* (2013.01); *A61B 18/22* (2013.01); *A61B 2017/00477* (2013.01); *A61B 2017/00734* (2013.01); *A61B 2017/00973* (2013.01); *A61B 2018/2065* (2013.01); *A61N 2005/063* (2013.01); *A61N 2005/067* (2013.01)
USPC ............... 385/91; 385/90; 385/134; 385/135; 606/15; 606/16

(58) Field of Classification Search
USPC ......... 385/88, 90, 91, 134, 135; 606/9, 15, 16
See application file for complete search history.

*Primary Examiner* — Melanie Hand
(74) *Attorney, Agent, or Firm* — CAO Group, Inc.

(57) ABSTRACT

Laser emission systems for surgical and other therapeutic uses are herein disclosed. In the preferred embodiments, different laser control systems are disclosed each capable of multiple, simultaneous emission of lasers of different wavelengths in a single beam. The embodiments feature a hand-held wireless laser module or a portable console with a laser tip extending therefrom. The laser module is controlled by wireless footswitch. Fiber extension modules may be used with the later embodiment.

8 Claims, 17 Drawing Sheets

(a)

(b)

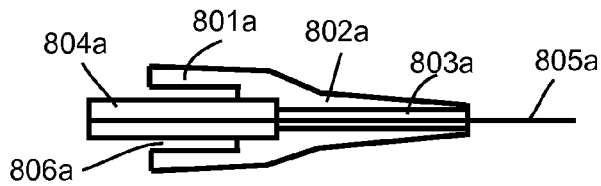
Fig. 8a. 0 degree tip
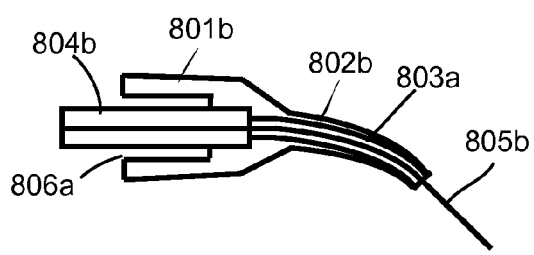
Fig. 8b. 30 degree tip
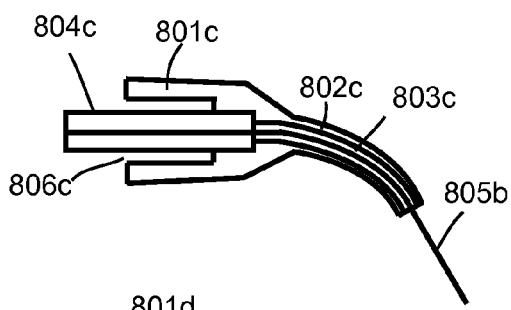
Fig. 8c. 45 Degree tip
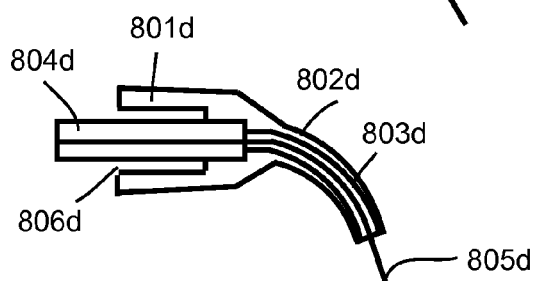
Fig. 8d. 60 Degree tip
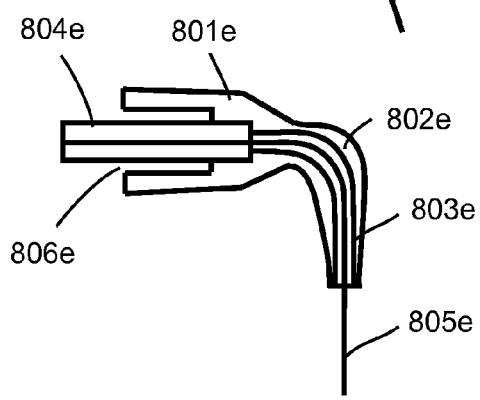
Fig. 8e. 90 Degree tip

MODULAR SURGICAL LASER SYSTEMS

CROSS-REFERENCES TO RELATED APPLICATIONS

This Application is a continuation application of U.S. application Ser. No. 12/035,427 filed on Feb. 21, 2008, which is a continuation-in-part of U.S. application Ser. No. 10/947,055 filed Sep. 22, 2004, now U.S. Pat. No. 7,485,116; and U.S. application Ser. No. 12/035,427 is also a non-provisional application of U.S. Application No. 60/891,037 filed on Feb. 21, 2007. Each of the above cross-referenced patent applications is hereby incorporated by reference in its entirety.

FIELD OF THE INVENTION

The present invention relates to the field of surgical and therapeutic devices and more particularly relates to the field of laser surgical and therapeutic devices.

BACKGROUND OF THE INVENTION

Surgical and therapeutic lasers using semiconductor laser as light source have been widely used in the medicine, dentistry and other areas. In order to increase the usage by practitioners, features of laser system need to be improved. A surgical laser with a fiber management system and disposable tips was described in the parent Application. The present invention, an improvement over the Parent, utilizes a modular system with wireless control, touch screen programming, a removable fiber cable, autoclaveable hand piece, and versatile surgical tips.

SUMMARY OF THE INVENTION

In view of the foregoing disadvantages inherent in the known types of laser systems, this invention provides an improved laser system with a laser module capable to provide multiple wavelengths, wireless remote control, an improved fiber optic coupling system for laser delivery, auto cleavable handpiece, replaceable tip structure. As such, the present invention's general purpose is to provide a new and improved laser system that is effective in use and easy and intuitive in that use.

To accomplish these objectives, the laser system according to the invention is practiced in two embodiments, both of which comprise a control module and a remote foot pedal operation control. In a first embodiment, the control module is a battery powered remote module which is easily maneuverable to a desired location. In the second, the control module is a relatively fixed consol and a separate handpiece is instead battery powered and movable. Both embodiments feature a laser module with multiple wavelength emission capability, a touch screen consol, a new fiber coupling system and replaceable therapeutic/surgical tips.

The more important features of the invention have thus been outlined in order that the more detailed description that follows may be better understood and in order that the present contribution to the art may better be appreciated. Additional features of the invention will be described hereinafter and will form the subject matter of the claims that follow.

Many objects of this invention will appear from the following description and appended claims, reference being made to the accompanying drawings forming a part of this specification wherein like reference characters designate corresponding parts in the several views.

Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in various ways. Also it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIGS. 8(a)-8(e) depict sample tips, of the design shown in FIG. 7b, set at different angles.

DETAILED DESCRIPTION OF THE PREFERRED EMBODIMENT

With reference now to the drawings, the preferred embodiment of the improved prophy cup is herein described. It should be noted that the articles "a", "an" and "the", as used in this specification, include plural referents unless the content clearly dictates otherwise.

Figure 1:
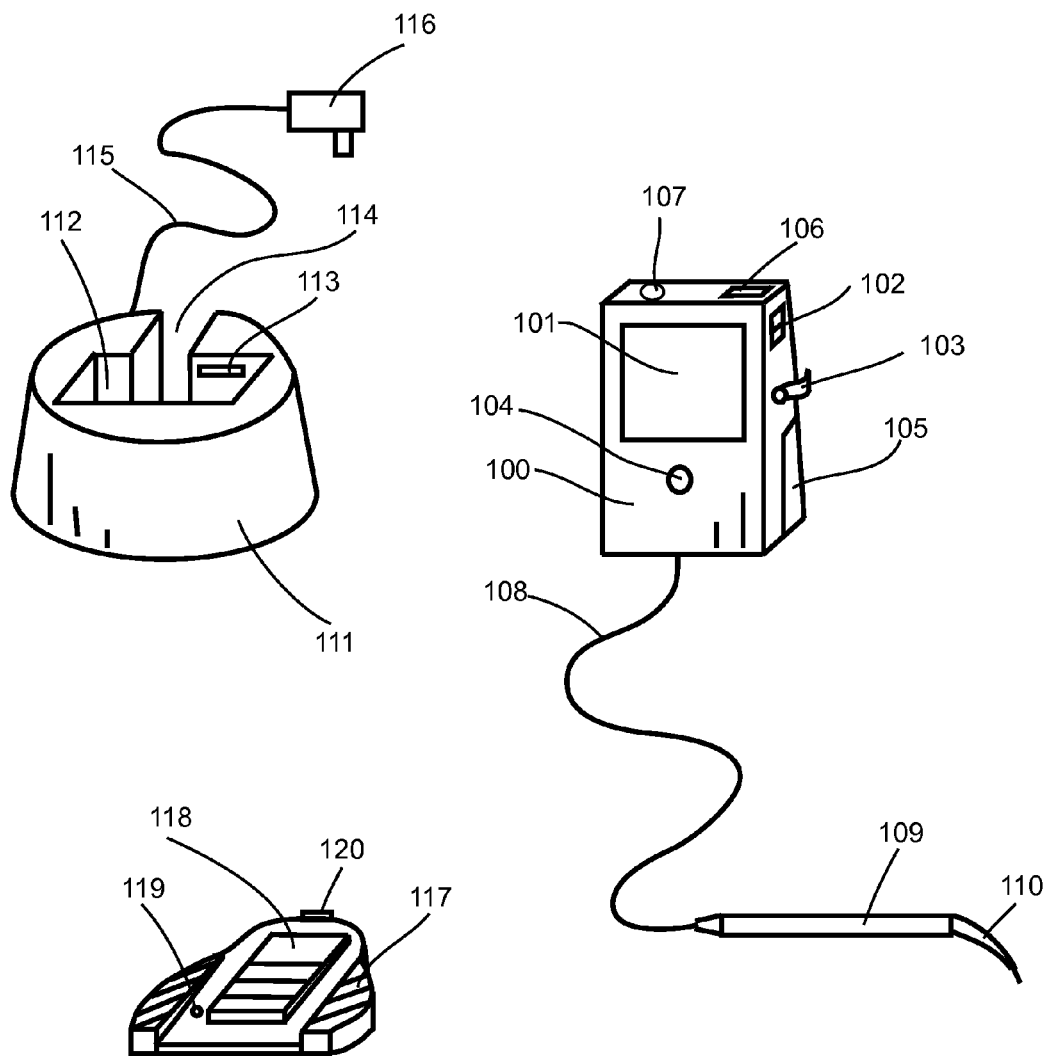
FIG. 1 is a plan view of the first embodiment of the surgical laser system according to the present invention.

FIG. 1 depicts a modular system laser with a main consol and a wireless footswitch where control consol 100 has a touch screen 101, a main electrical switch 102, a handpiece holder 103, an emergency stop button 104, a battery pack 105 to make the unit operable by battery, a USB port 106 to update system operating software, a remote control port 107 to control laser emission remotely if needed, a fiber cable 108 extending from control consol 100, a handpiece 109 connected to fiber cable 108 generally opposite the consol 100 and a disposable tip 110 connected to handpiece 109. The preferred embodiment of the system as a whole likewise comprises a cradle 111 to house the control consol 100. The cradle 111 has an open slot 112 for consol 100 to sit. A connection pin 113 is disposed within the slot 112 to connect electrical power from cradle 111 to control con sol 100. There is a secondary slot 114 to allow fiber cable in the con sol 100 to go through cradle 111 when the consol 100 sits in the cradle. An electrical cord 115, with an appropriate power supply 116, is connected to the cradle 111 and is in operable connection to the connector pin 113. The electrical power supply 116 and 115 can also connect to consol 100 directly without a cradle. The preferred embodiment of the system also comprises a wireless footswitch 117 to control the laser emission. The wireless footswitch contains a footswitch 118, a multiple color LED indicator 119 for battery and signal status, and a reset button 120.

Figure 2:
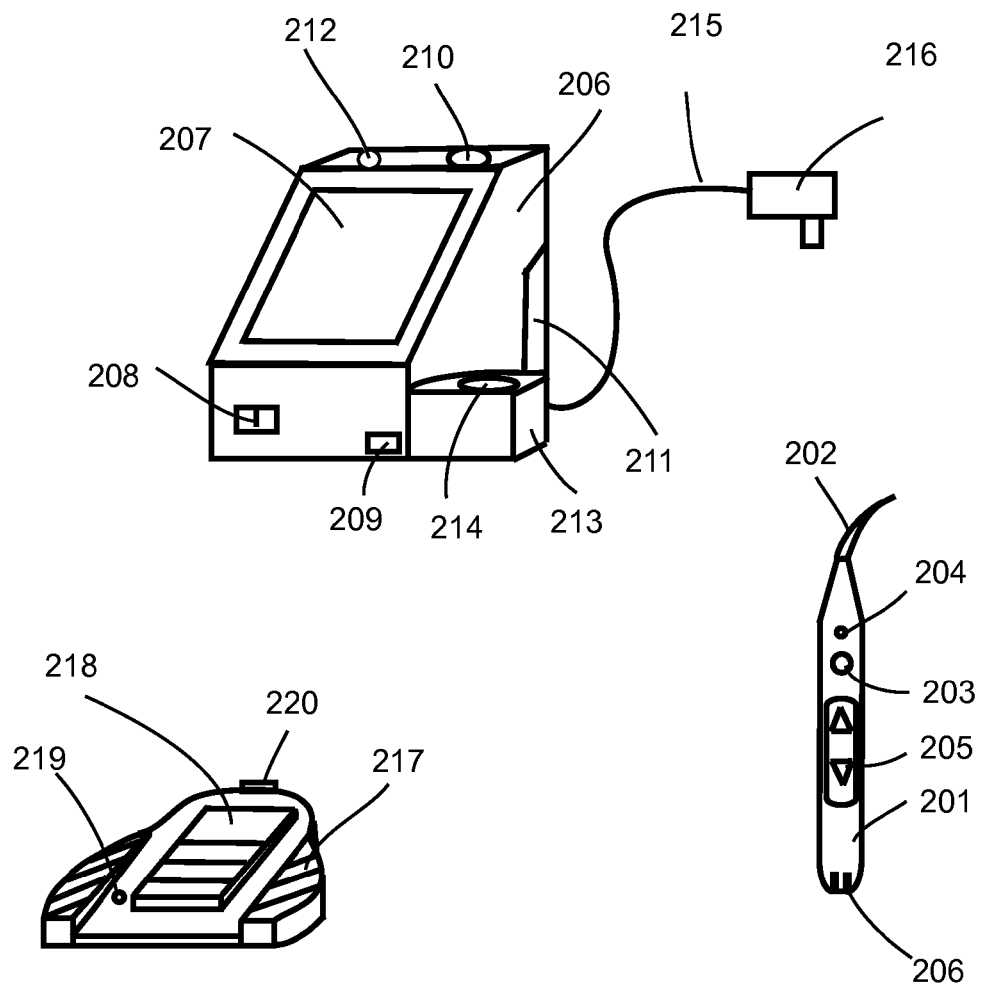
FIG. 2 is a plan view of a second embodiment of the invention, utilizing a wireless handpiece.

In FIG. 2, the laser system has a wireless laser handpiece 201 with a disposable tip 202. The handpiece 201 is battery operated. Handpiece 201 also features an emergency stop button 203 and a laser emission indicator 204. There is also a laser intensity adjustment control 205 on the laser handpiece 201. Like the previous embodiment, the system contains a control consol 206 with a touch screen 207, a main power switch 208, a USB port 209 for programming updates, an emergency stop button 210, a battery pack 211 and a remote control switch 212. In this embodiment, the consol 206 also comprises a hand piece holder 213, an open slot 214 in 213 for handpiece to sit, a removable electrical cable 215 attached to control consol 206 for charging purposes (actual connection means between the cable 215 and the open slot 214, for charging the handpiece 201, is not shown), and a switch power supply 216 to provide electrical power. The system also include a wireless footswitch 217 including a main footswitch 218, a multiple color LED indicator 219 for battery and signal status and a reset button 220.

Figure 3:
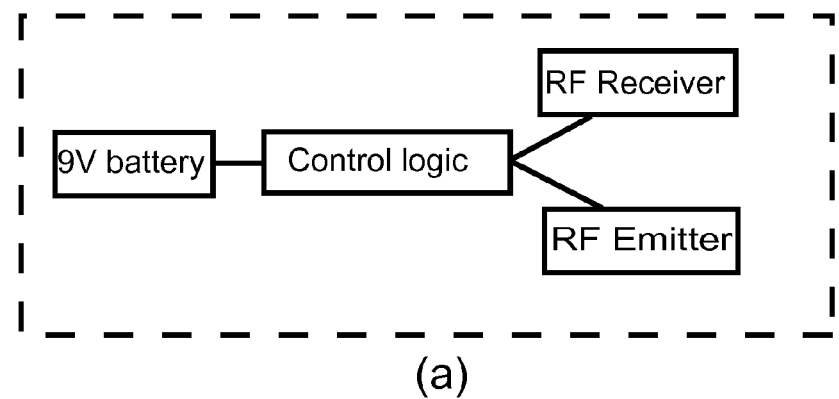
FIG. 3 depicts electronic architect of modular laser system illustrated in FIG. 1.
Figure 3:
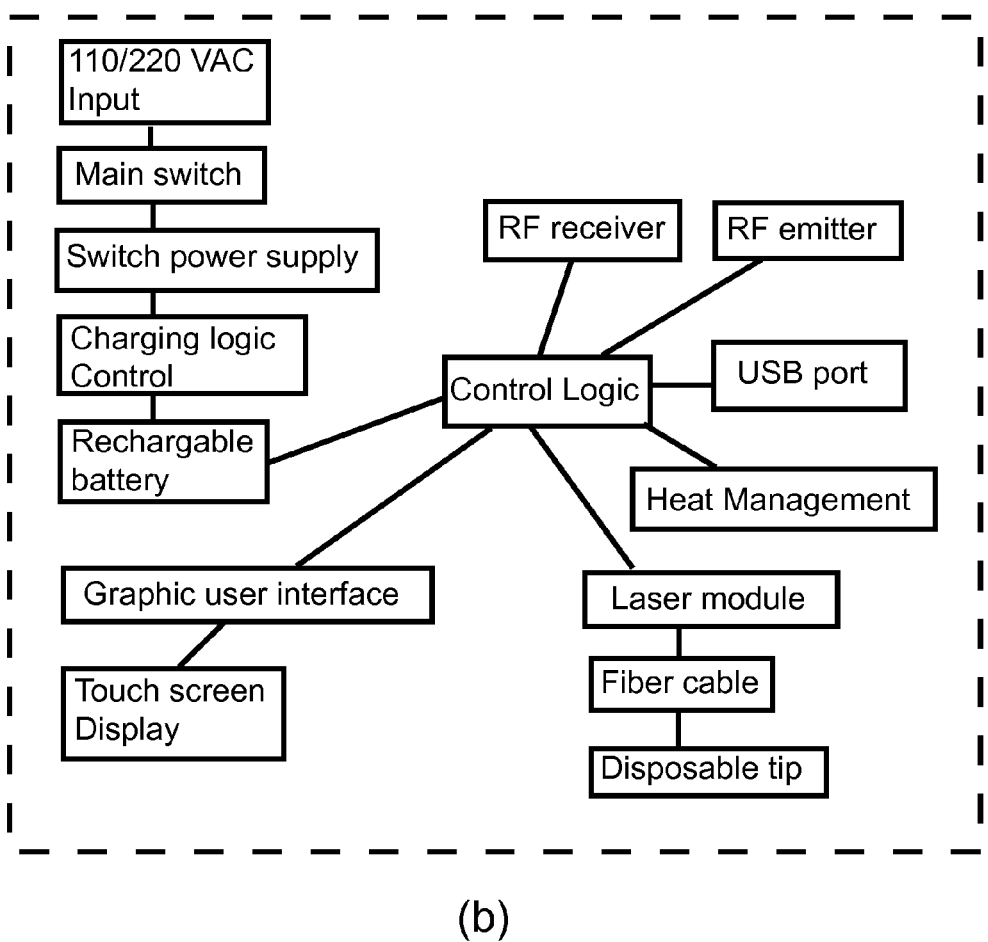

FIG. 3 depicts the electrical architecture of the first embodiment where block (a) contains electrical design for wireless footswitch. The footswitch is powered by battery and is operated by a control logic circuit which process signals for an electronic signal emitter and receiver (denoted as ES receiver and ES emitter in the Figures). It should be noted that, as used in this Application, the term "electronic signal" includes any means of wireless communication now known or later developed, including but not limited to Laser, IR, RF, and BLUETOOTH communications. Block (b) illustrates the architectural design for main control. There is a battery charging section as the unit is operated by battery. The signal is processed through control logic circuit. The information is input by touch screen through a graphic user interface. The signal from foot switch controls laser emission by sending electronic signals to the system as a whole. The control program can be updated through a USB port.

Figure 4:
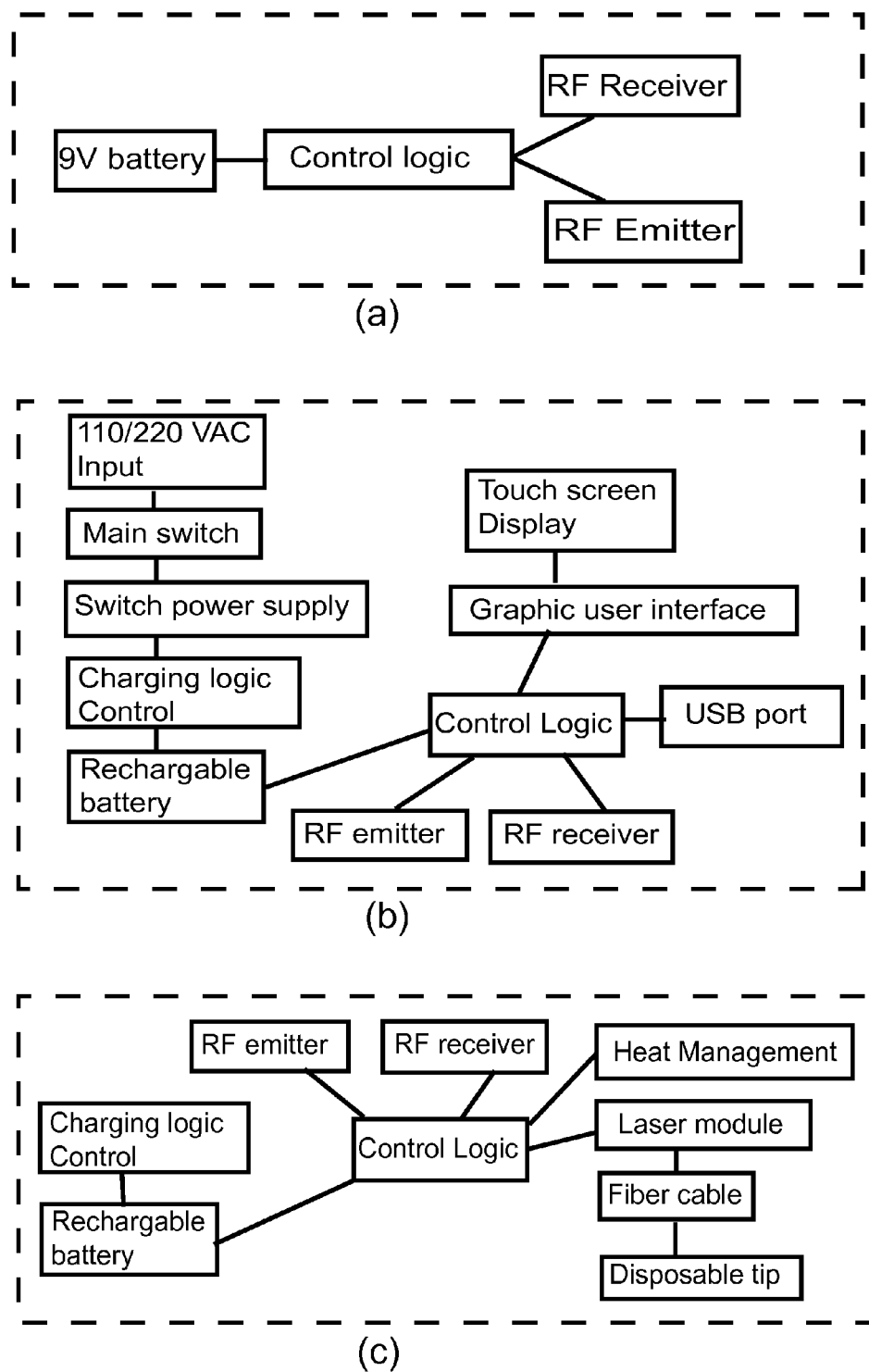
FIG. 4 depicts electronic architect of modular laser system illustrated in FIG. 2.

Similarly in FIG. 4, where the architecture is for the system in FIG. 2, block (a) illustrates electrical design for wireless footswitch. The footswitch is powered by battery to operate a control logic which process signals for the electronic signal emitter and receivers. Block (b) illustrates the architectural design for main control. There is a battery charging section as the control console and handpiece are operated by battery. The signal is processed through a control logic circuit. The information is inputted by touch screen through a graphic user interface. The control program can be updated by a USB port. Block (c) illustrates the architect design for a laser handpiece which is operated by battery. There is an electronic signal emitter and receiver in the handpiece to receive/send signals from and to main control unit. The information is processed by control logic circuit to control laser emission. The laser emission is controlled by wireless signal from footswitch.

Figure 5:
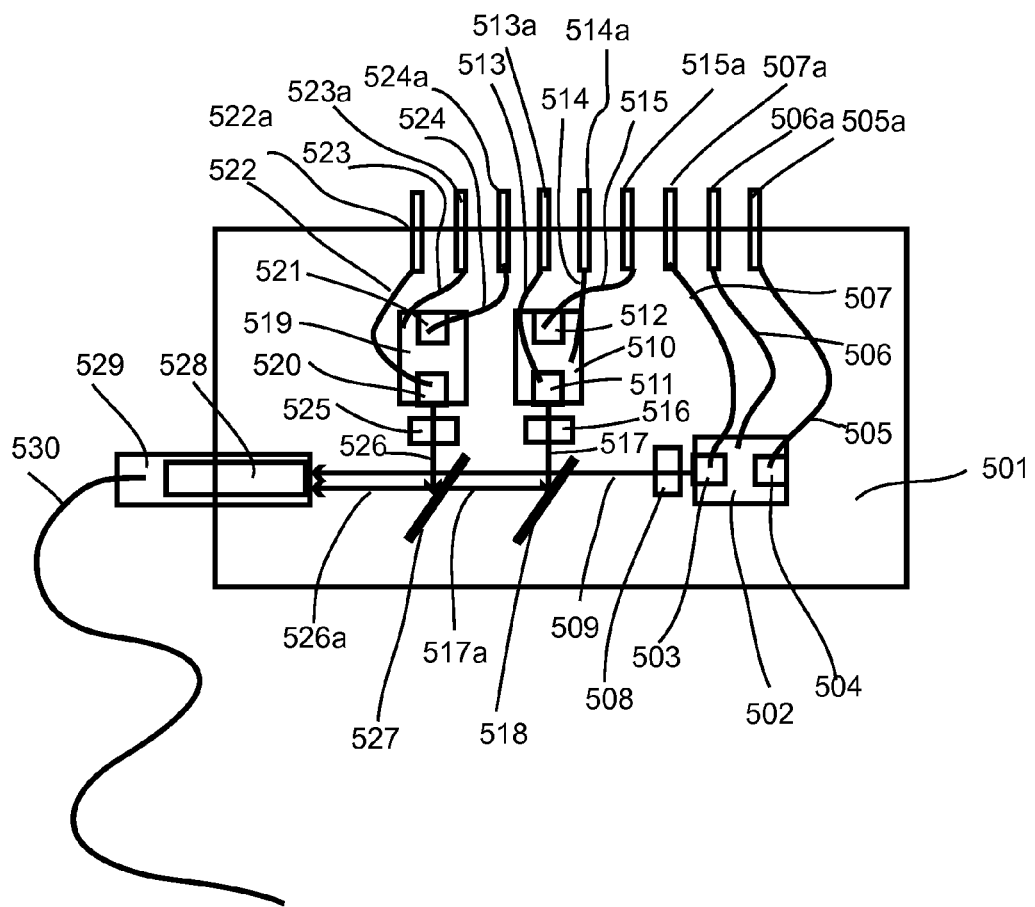
FIG. 5 is a schematic depicting a laser module to provide multiple wavelengths for the laser system.

Both embodiments use a laser module to generate a multiple wavelength laser beam for emission through a single fiber. It should be noted that the laser module is located in the consol in the first embodiment (FIG. 3) and the handpiece in the second (FIG. 4). FIG. 5 depicts a laser module used in both embodiments. The laser module depicted in FIG. 5 can be either a laser module capable of emitting a single wavelength or multiple wavelengths, dependent upon the types of laser chips used in the module. The laser module is encased in a metal housing 501. Inside housing 501, a heat sink 502 carries a laser chip 503 and a detector chip 504. The detector chip 504 detects the laser signal so that the emission of laser power can be controlled. The laser chip 503 and detector chip 504 are bonded by conduction wires 505, 506, 507 respectively to the electrodes 505*a*, 506*a*, and 507*a* on the housing 501, respectively. In front of laser chip 504, there is an optical lens 508 to make the emitted laser beam become a parallel beam 509 for transport.

Another heat sink 510 carries a laser chip 511 and a detector chip 512. The laser chip and detector chips are bonded by conduction wires 513, 514, and 515 to the electrodes 513*a*, 514*a*, and 515*a* respectively. There is an optical lens 516 to make the emitted laser beam become a parallel beam 517. Both beam 509 and 517 meet with a filter/reflector 518 which is 100% transparent to beam 509 and 100% reflective to beam 517, reflecting beam 517 to make create beam 517*a*. The reflectivity and transparency of this filter/reflector 518 is due to one side of the filter/reflector 518 being transparent to all or at least most wavelengths of laser light while the other is reflective of all or most wavelengths of laser light.

Yet another heat sink 519 carries laser chip 520 and detector chip 521. The laser chip and detector chips are bonded by conductive wires 522, 523, and 524 to the electrodes 522*a*, 523*a*, and 524*a* respectively. There is an optical lens 525 to make the emitted laser beam become a parallel beam 526. Beam 526, 509, 517*a* meet with a filer/reflector 527 which are 100% transparent to 509 and 517*a* and 100% reflective to beam 526, reflecting bean 526 to create beam 526*a*. All three beams, 509, 517*a*, 526*a* reach an optical lens 528 housed by holder 529. Lens 528 focuses all three beams into a single fiber 530. Thus, with three generated laser beams merged into a single beam, the fiber can emit a single laser beam with three different wavelengths. It is conceivable that additional laser sources may be used to add more wavelengths to the final emitted beam.

Delivering a laser beam to a surgical surface is a key for the laser system. Several laser beam delivery mechanisms will be disclosed herein.

FIG. 6(*a*) describes one of the delivery mechanisms for a laser beam. Given a laser module 6001 as described in FIG. 5, the system according to the present invention is then assembled with the laser module 6001 as a centerpiece, shown in FIG. 6(*a*). Fiber 6002 exits module 6001 to connect to other components. A ferrule 6003 is provided to the fiber 6002 so as to connect the fiber 6002 to the next stage. A nut 6004 connected to ferrule 6003 facilitates the connection of ferrule 6003 to other connections. The fiber 6002 is finished at end of ferrule 6005 with standard fiber finish. Then, there is a housing 2007 with an opening 2008 at proximal end and another opening 2009 at distal end. There are precision spacers 2010 and 2011 at both ends of an optical lens 2012, inside housing 2007. The details for housing 6007 will be described in FIG. 6(b). A coupler 6013 is provided for further light transportation. The coupler 6013 with opening 6014 at proximal end opening 6015 at distal end, and a stop point 6016 contains housing 2007. Then, a ferrule 6017 contains another fiber 6018. A nut 6019 is connected to 6017 for attachment. Fiber 6018 has a standard finish 6020 for at end 6017. At another end of fiber 6018, there is a ferrule 6021 to make fiber to connect to next stage. A nut 6022 is attached to ferrule 6021 and a fiber finish surface 6023 at end of ferrule 6020. Another housing 6024 with opening 6025 at proximal end and opening 6026 at distal end contains a precision spacer 6027 and 6028 at both end of an optical lens 6028, respectively. A coupler 6030 with opening 6031 at proximal end, opening 6032 at distal end, and a stop point 6033 to house 6024. Another ferrule 6034 to contain fiber 6035 with fiber finish 6036 can be fit to coupler 6030.

Figure 6A:
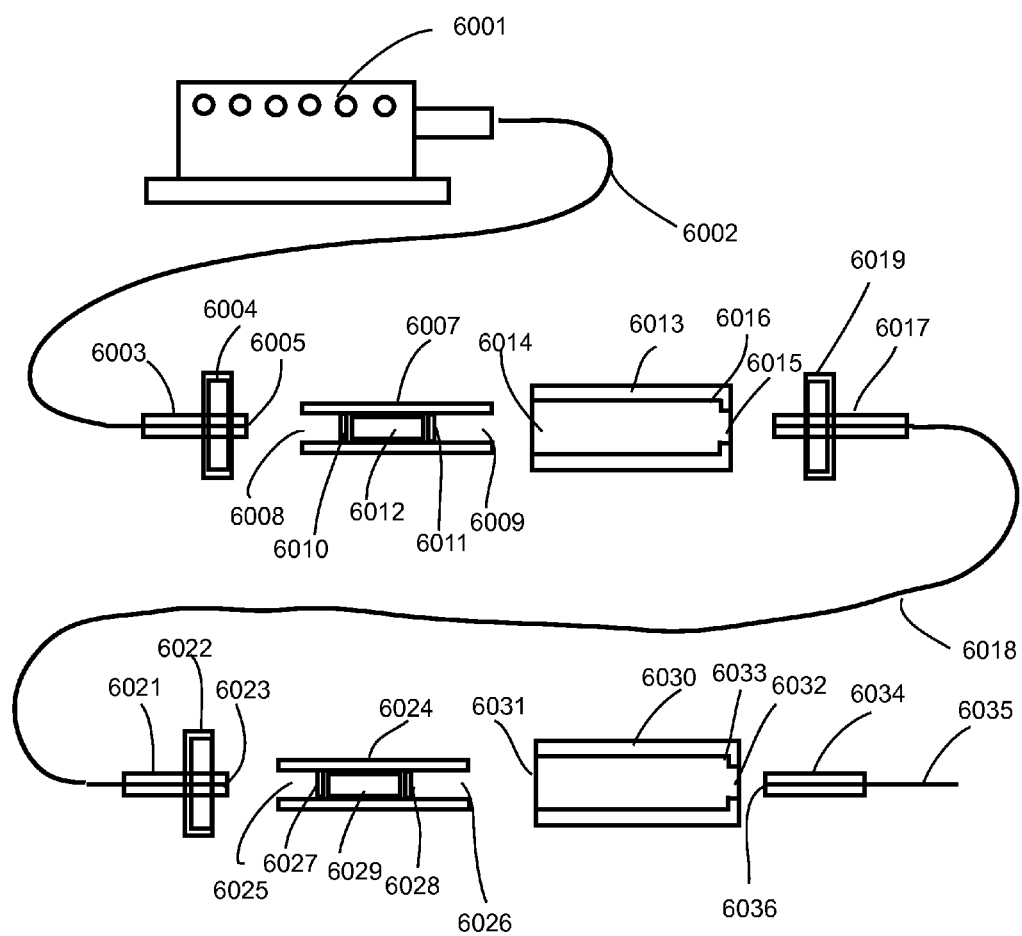
FIG. 6(a) is a schematic depicting one of laser beam delivery mechanism designed for laser system.
Figure 6B:
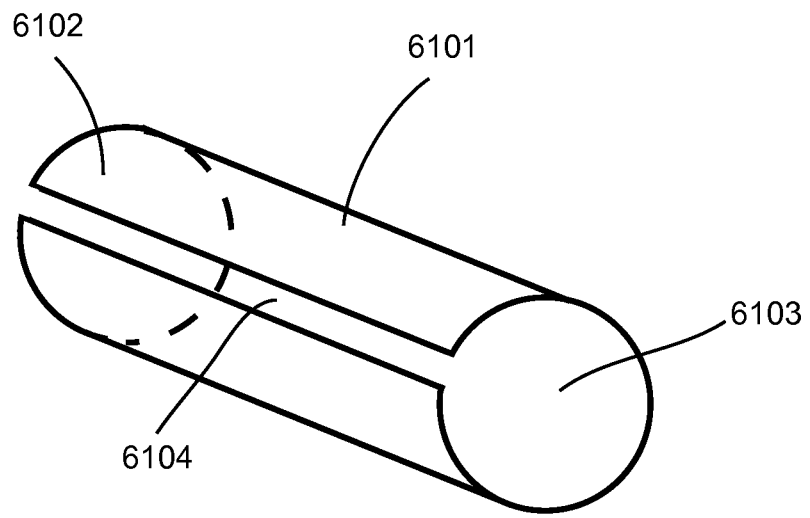
FIG. 6(b) depicts a coupler housing

FIG. 6(b) depicts details the housing 6007 and 6024. A cylindrical housing 6101 which can be made of metal or plastic with elastic properties has an opening 6102 at proximal end, opening 6103 at distal end, and an open slot 6104 from proximal end to distal end. The important feature is the open slot 6104 to allow any ferrules with size larger than inside diameter of 6101 to get in from both ends and to automatically align the ferrules. This is important to accommodate the variance of the ferrule, as even they are in precise relation to each other.

Figure 6C:
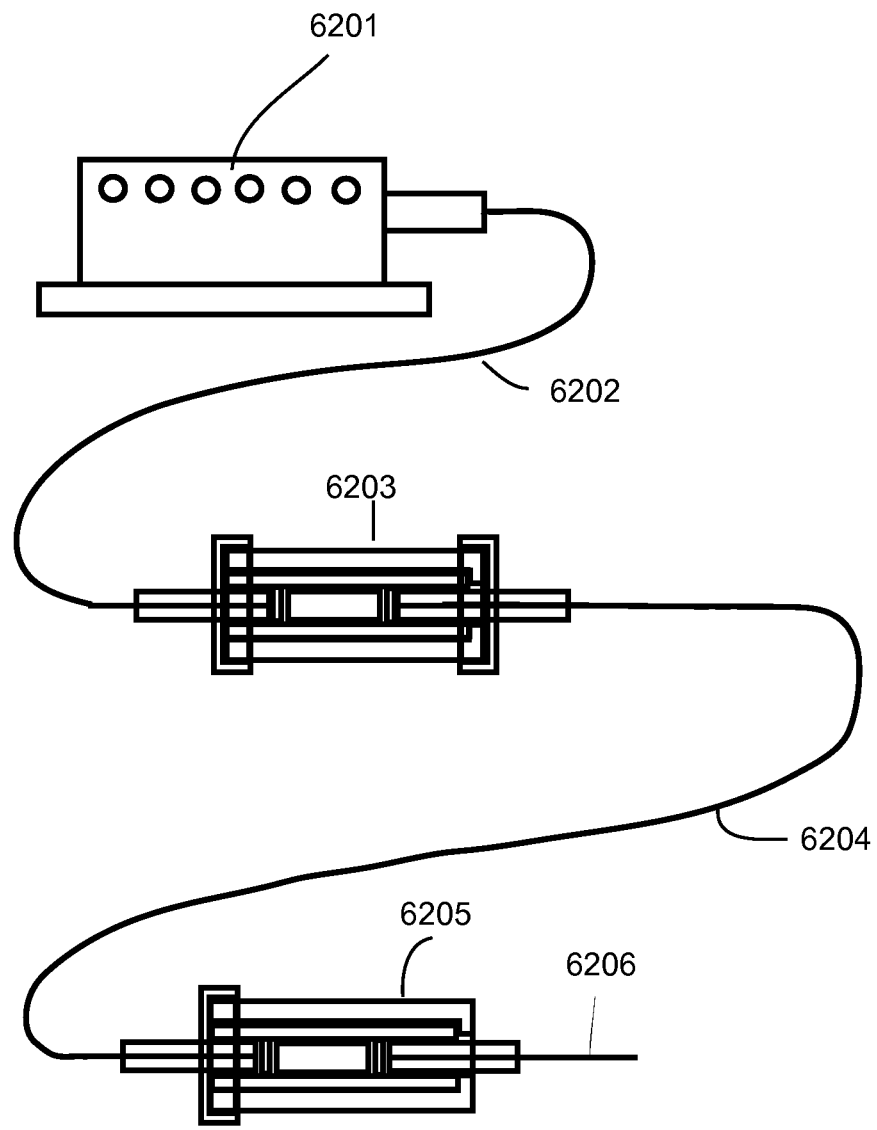
FIG. 6(c) depicts the assembled laser beam delivery in FIG. 6a FIG. 6(d) depicts the optical beam trace mechanism for laser beam delivery described in FIG. 6(a).

FIG. 6(c) depicts assembled fiber conduction mechanism as layout in FIG. 6(a). A laser beam from laser module 6201 is transported through a fiber cable 6202 to a connection point 6203, which contains a coupler, a housing with one lens and spacers, and a ferrule for another fiber 6204. The laser beam is coupled from one fiber to another fiber utilizing connection points 6203. The mechanism of coupler, spacers and lens make the coupling efficiency from one fiber to another fiber to the optimum. The connection 6203 can be the transporting point to transport laser beam from inside the laser system to outside the laser system as depicted in FIG. 1 and FIG. 2 Then, laser beam is transported to another connection point 6205, contains a coupler, a housing with one lens and spacers, and a ferrule for another fiber 6206, which may deliver the laser beam to the surgical surface. The connection point 6205 can also be the transporting point from the handpiece to the replaceable tip for laser system as depicted in FIG. 1 and FIG. 2.

Figure 6D:
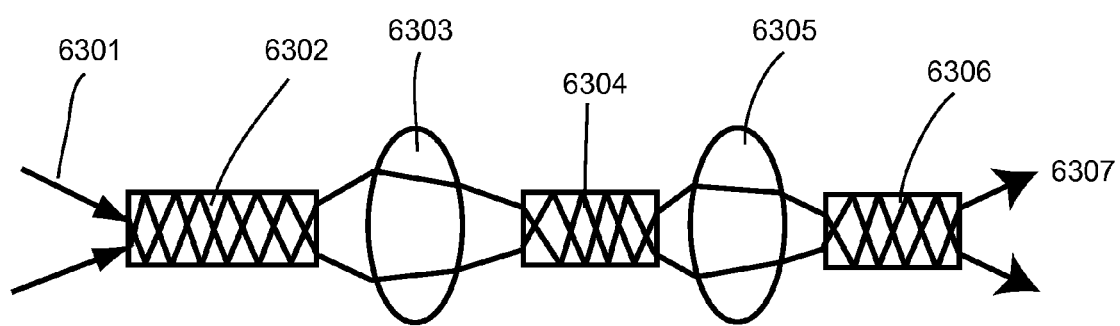
FIG. 6(e) depicts a different laser beam delivery mechanism for designed laser system.
FIG. 6(f) depicts the assembled laser beam deliver in FIG. 6e.
FIG. 6(g) depicts the optical beam trace mechanism for laser beam delivery described in FIG. 6e.
FIG. 6(h) depicts another laser beam delivery system.
FIG. 6(i) depicts assembled laser beam delivery described in FIG. 6h.
FIG. 6(j) depicts the optical beam trace mechanism for laser beam delivery described in FIG. 6h.

FIG. 6(d) depicts the optical system for laser transportation described in FIG. 6(a). A laser beam 6301 inputs to a fiber 6302, then exits from fiber 6302, then focused by lens 6303 to another fiber 6304, then exits fiber 6304, then focused by lens 6305 to another fiber 6306, finally exits at end of 6306 as a beam 6307 to an application surface.

The laser beam deliver mechanism depicted in FIG. 6(d) can be used for a laser system with power output range from 1 to 10 watt.

Figure 6E:
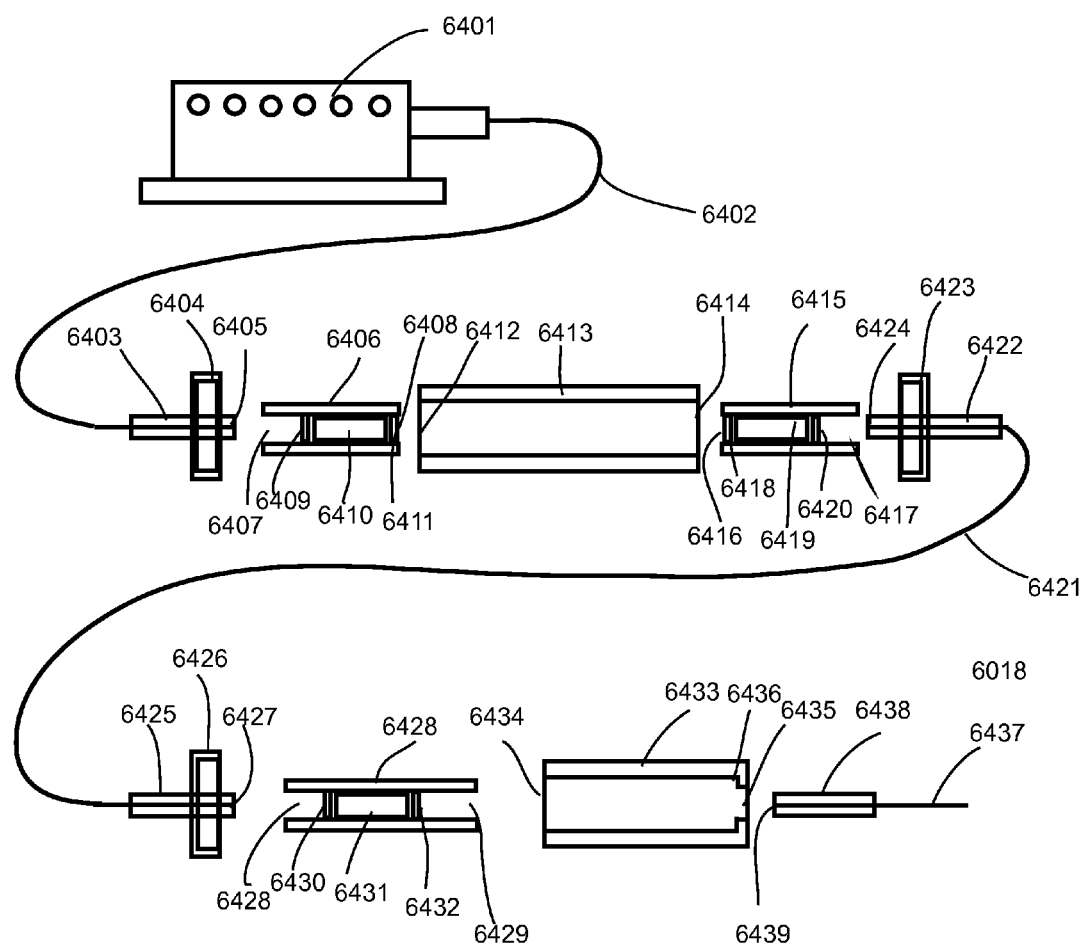

FIG. 6(e) describes another of the delivery mechanisms for a laser beam. Given a laser module 6401 as described above, the system according to the present invention is then assembled with the laser module 6401 as a centerpiece, shown in FIG. 6(e). Fiber 6402 exits module 6401 to connect to other components. A ferrule 6403 is provided to the fiber 6402 so as to connect the fiber 6402 to the next stage. A nut 6404 connected to ferrule 6403 facilitates the connection of ferrule 6403 to other connections. The fiber 6402 is finished at end of ferrule 6405. Then, there is a housing 2406 with an opening 2407 at proximal end and another opening 2408 at distal end. There is a precision spacer 2409, an optical lens 2410, and another precision spacer 2411 inside housing 2406. The housing 6406 is identical to housing 6007 described in FIG. 6(b). A coupler 6413 is provided for further light transportation. The coupler 6413 with opening 6412 at proximal end opening 6414 at distal end. While housing 6406 is inserted within coupler 6413 at proximal end 6412, an identical housing 6415 is likewise inserted into coupler distal end 6414. The structure inside housing 6415 mirrors the structure in housing 6406 in that it contains a precision spacer 2418, an optical lens 2419, and another precision spacer 2420 inside housing 6415. Housing 6415 also presents proximal opening 6416 and distal opening 6417. Distal opening 6417 receives a ferrule 6422 containing fiber 6421, which is finished at the end of ferrule 6424. Ferrule 6422 likewise is attached to a nut 6423 to facilitate connection. This is the first part of connection fiber 6421, which has an identical structure at its other end, specifically there is a ferrule 6425 to make fiber to connect to next stage. A nut 6426 is attached to ferrule 6425 and a fiber finish surface 6427 at end of ferrule 6425. Another housing 6428 with opening 6429 at proximal end and opening 6430 at distal end contains a precision spacer 6431, and lens 6432, and a precision spacer 6433. A coupler 6434 with opening 6435 at proximal end, opening 6436 at distal end, and a stop point 6437 to house 6428. Another ferrule 6439 to contain fiber 6438 with fiber finish 6440 can be fit to coupler 6434. This construction had the added utility of an extra focusing lens over the first embodiment described in FIG. 6(a).

Figure 6F:
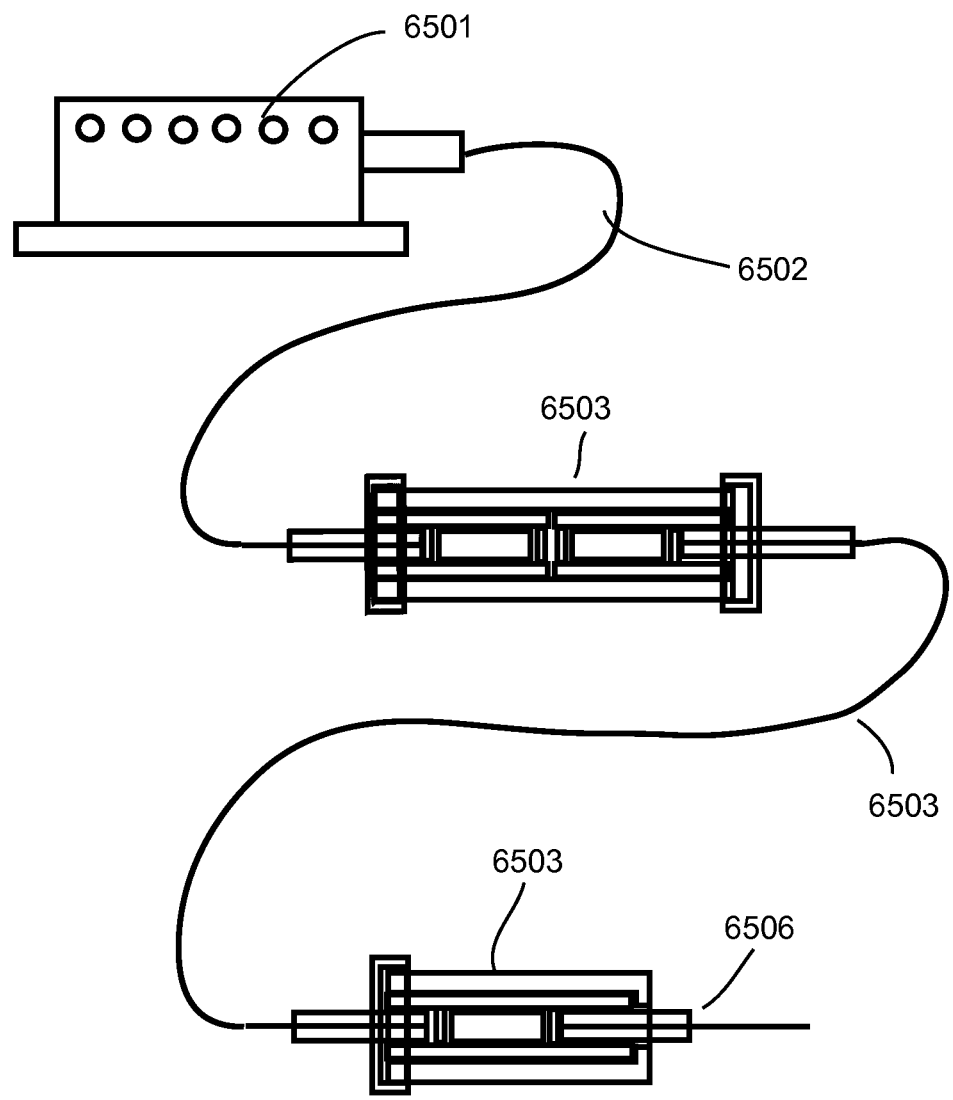

FIG. 6(f) depicts assembled fiber conduction mechanism as layout in FIG. 6(e). A laser beam from laser module 6501 is transported through a fiber cable 6502 to a connection point 6503, which contains a coupler, a housing with two lenses, and a ferrule for another fiber 6504. The connection point 6503 can also be the transporting point to transport laser beam from inside the system to the outside the system as depicted in FIG. 1 and FIG. 2. Then, laser beam is transported to another connection point 6505, contains a coupler, a housing with one lens, and a ferrule for another fiber 6506, which may deliver the laser beam to the surgical surface. The connection point 6506 can be the transporting point from the handpiece to the replaceable tip for laser system as depicted in FIG. 1 and FIG. 2.

Figure 6G:
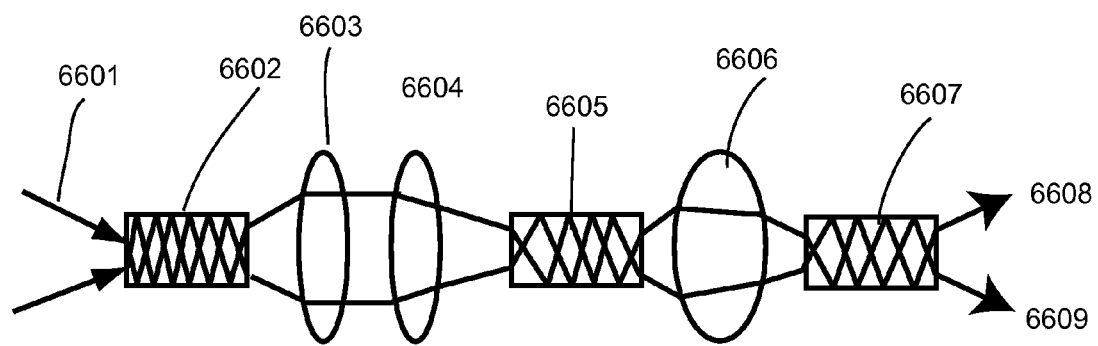

FIG. 6(g) depicts the optical system for laser transportation described in FIG. 6(e). A laser beam 6601 inputs to a fiber 6602, then exits from fiber 6602, then focused by lenses 6603 and 6604 to another fiber 6605, then exits fiber 6605, then focused by lens 6606 to another fiber 6607, finally exits at end of 6607 as a beam 6608 to an application surface.

The laser beam deliver system depicted in FIG. 6(g) can be used for a laser system with moderate power output, for example, the final laser output is ranged from 1 to 15 watt.

Figure 6H:
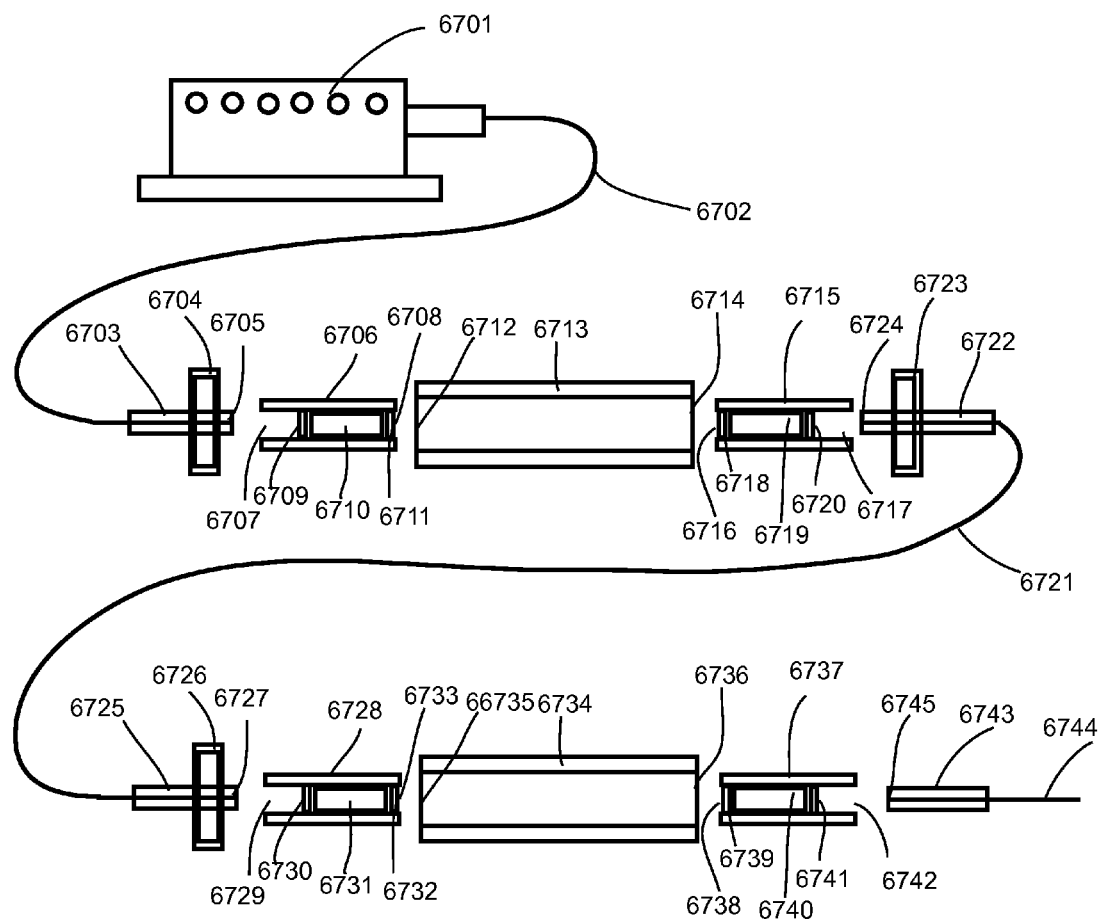

FIG. 6(h) describes another of the delivery mechanisms for a laser beam. Given a laser module 6701 as described above, the system according to the present invention is then assembled with the laser module 6701 as a centerpiece, shown in FIG. 6(h). Fiber 6702 exits module 6701 to connect to other components. A ferrule 6703 is provided to the fiber 6702 so as to connect the fiber 6702 to the next stage. A nut 6704 connected to ferrule 6703 facilitates the connection of ferrule 6703 to other connections. The fiber 6702 is finished at end of ferrule 6705. Then, there is a housing 2706 with an opening 2707 at proximal end and another opening 2708 at distal end. There is a precision spacer 2709, an optical lens 2710, and another precision spacer 2711 inside housing 2706. The housing 6706 is identical to housing 6007 described in FIG. 6(b). A coupler 6713 is provided for further light transportation. The coupler 6713 with opening 6712 at proximal end opening 6714 at distal end. While housing 6706 is inserted within coupler 6713 at proximal end 6712, a housing 6715 is likewise inserted into coupler distal end 6714. The structure inside housing 6715 mirrors the structure in housing 6706 in that it contains a precision spacer 2718, an optical lens 2719, and another precision spacer 2720 inside housing 6715. Housing 6715 also presents proximal opening 6716 and distal opening 6717. Distal opening 6717 receives a ferrule 6722 containing fiber 6721, which is finished at the end of ferrule 6724. Ferrule 6722 likewise is attached to a nut 6723 to facilitate connection. This is the first part of connection fiber 6721, which has an identical structure at its other end, specifically there is a ferrule 6725 to make fiber to connect to next stage. A nut 6726 is attached to ferrule 6725 and a fiber finish surface 6727 at end of ferrule 6725. Another housing 6728 with opening 6729 at proximal end and opening 6733 at distal end contains a precision spacer 6430, an lens 6431, and a precision spacer 6432. A coupler 6734 is provided for further light transportation. The coupler 6734 with opening 6735 at proximal end opening 6736 at distal end. While housing 6728 is inserted within coupler 6734 at proximal end 6735, an identical housing 6737 is likewise inserted into coupler distal end 6736. The structure inside housing 6737 mirrors the structure in housing 6728 in that it contains a precision spacer 2738, an optical lens 2740, and another precision spacer 2741 inside housing 6737. Housing 6737 also presents proximal opening 6738 and distal opening 6742. Distal opening 6742 receives a ferrule 6743 containing fiber 6744, which is finished at the end of ferrule 6745. This construction had the added utility of an two extra focusing lenses over the first embodiment described in FIG. 6(a).

Figure 6I:
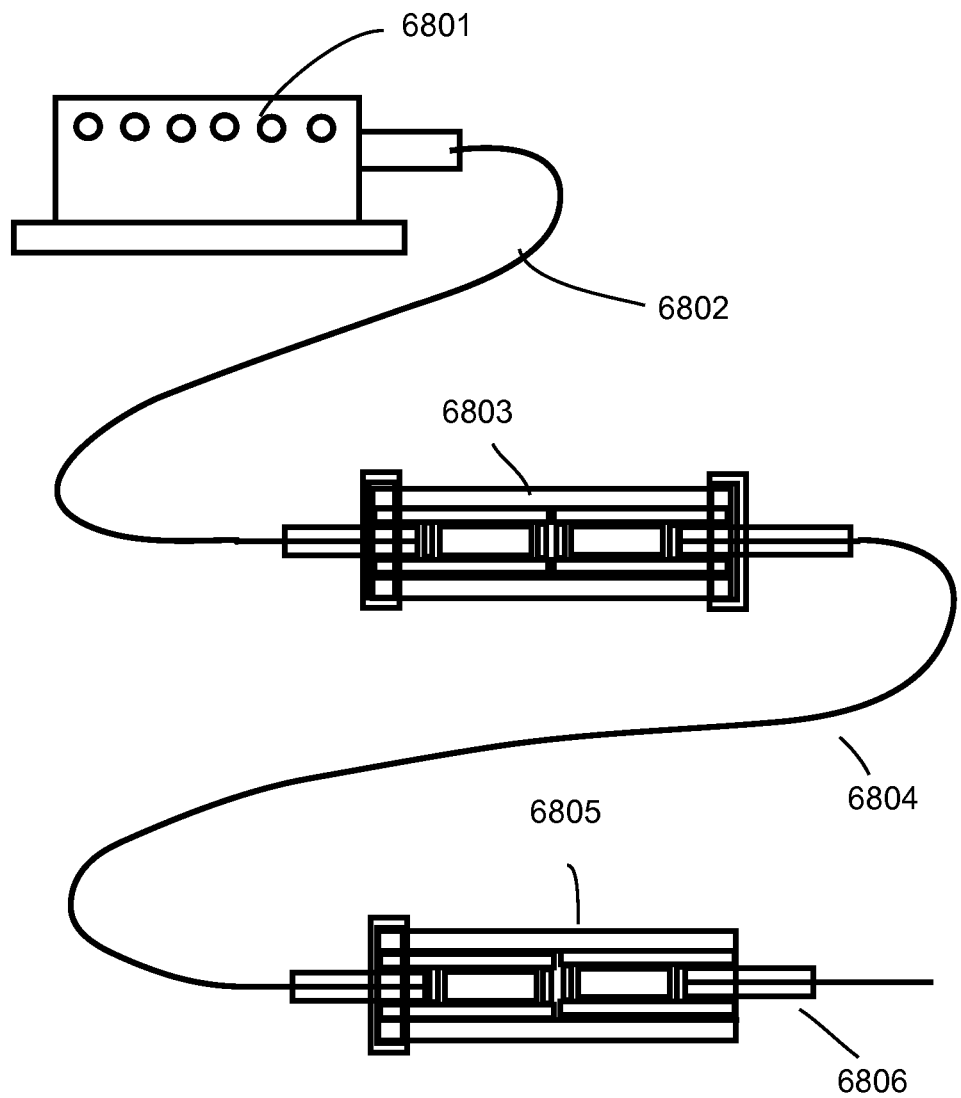

FIG. 6(i) depicts assembled fiber conduction mechanism as layout in FIG. 6(h). A laser beam from laser module 6801 is transported through a fiber cable 6802 to a connection point 6803, which contains a coupler, a housing with two lenses, spacers between lens and fiber finishes, and a ferrule for another fiber 6804. Then, laser beam is transported to another connection point 6805, contains a coupler, a housing with two lenses, and a ferrule for another fiber 6806.

Figure 6J:
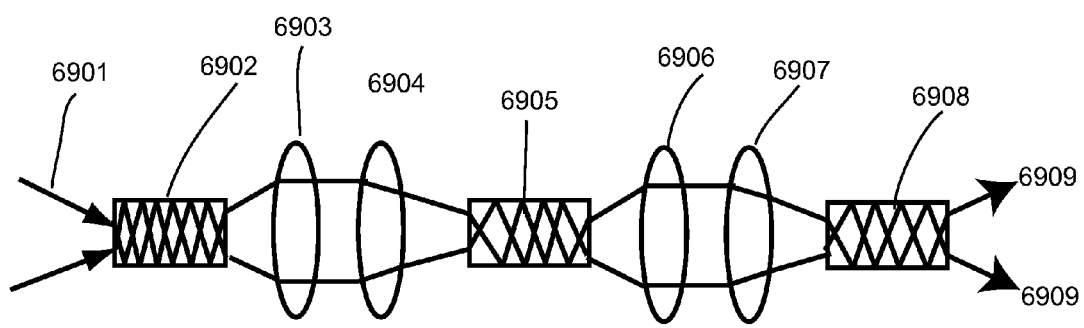

FIG. 6(j) depicts the optical system for laser transportation described in FIG. 6(h). A laser beam 6901 inputs to a fiber 6902, then exits from fiber 6902, then focused by lenses 6903 and 6904 to another fiber 6905, then exits fiber 6905, then focused by lenses 6906 and 6907 to another fiber 6608, finally exits at end of 6608 as a beam 6609 to an application surface. The mechanism designed in FIG. 6(j) can be useful for high power laser delivery.

Figure 7A:
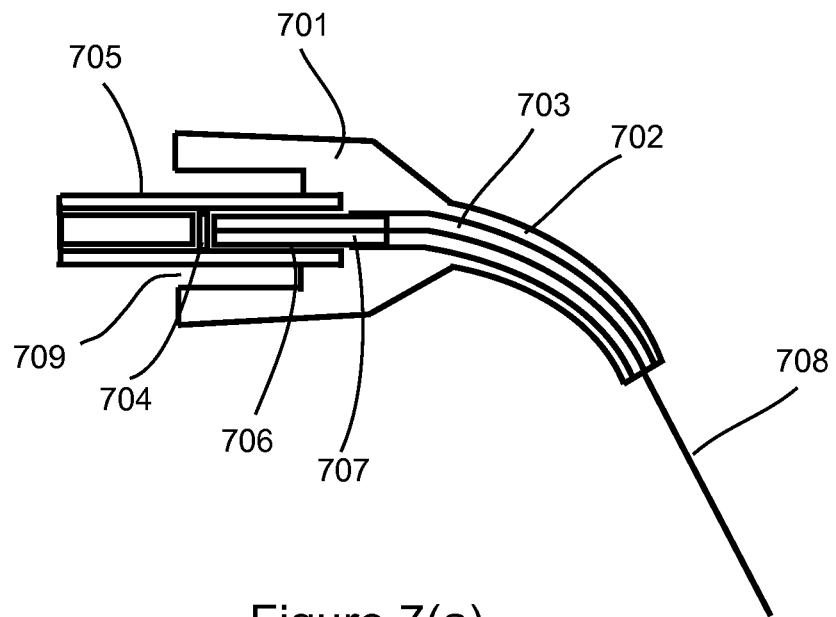
FIGS. 7(a) and 7(b) are schematics depicting alternate laser tips for the present invention.

Due to the fiber coupling design in FIGS. 6(a)-6(j), the fiber tips for surgical purpose can be changed at any given time. A tip design with a housing and an optical lens is illustrated in FIG. 7a. The tip comprises a casing 701 from which cannular tip 702 extends. In the cannular tip 702, there is a channel 703 to guide fiber 708. A cylindrical housing 704 contains an optical lens 705, a spacer 706 and a fiber connector 707 which encompasses one end of fiber 708. The fiber 708 will be bent according to the shape of channel 703 which can be straight or any angle. There is an open space 709 so that the tip can fit to the designated handpiece.

Figure 7B:
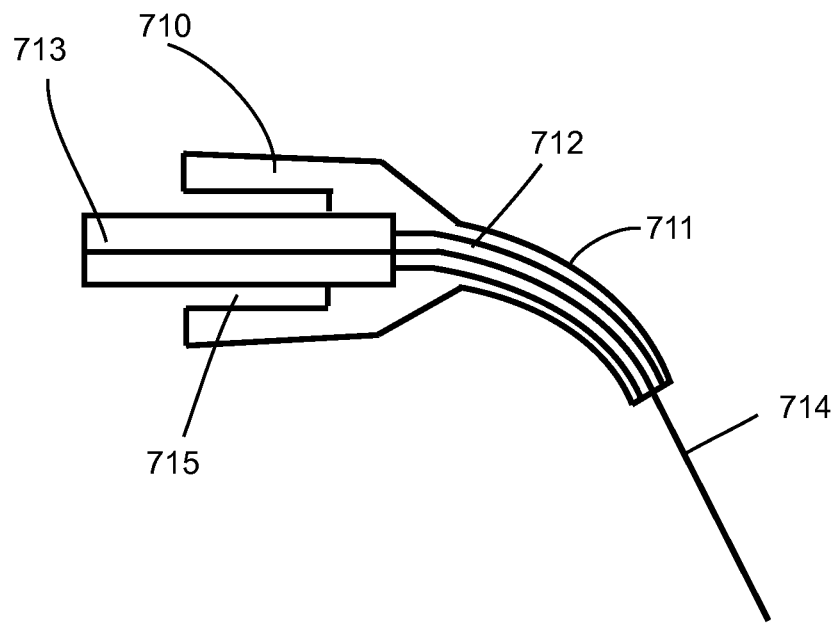

The tip shown in FIG. 7b is a tip without an optical lens. Tip comprises casing 710 from which cannular tip 711 extends. In cannular tip 711, there is a channel 712 to guide fiber 714. There is a connector 713 encompassing fiber 714 inside tip casing 710. The cannular tip 711 can be any angle by designing the casing so that the fiber can be any angle relative to tip axis. There is a space 715 to have tip to fit into handpiece. In either tip embodiment, the fiber in the tip can be versatile and may emit light in different patterns through the physical structure of the tip, as is known in the art and later discovered, including just at the end of the tip or in all directions. The structure of the tip is such that the fiber 708, 714 is fixedly encased in the tip, with the intention of being disposable while sacrificing as little material resources as possible. By being fixed in the tip and disposable, do not suffer the same stresses as other prior art fibers and can be gently bent to any angle during assembly with little fear of stresses and strain caused by repeated insertion and removal of fibers into other cannula systems.

Tips may be offset at any angle from an axis defined by the fiber connectors in the tip. FIGS. 8a-8e depict the tip design of FIG. 7b with offsets of 0°, 30°, 45°, 60° and 90° respectively. These angles are of course examples as any angle may be used since casing of each tip supports the fiber and the fiber is not stressed by being repeatedly bent to various degrees when inserted and removed from a cannula or other guide. Each tip has a casing 801a, 801b, etc. with a cannular tip 802a, 802b, etc. extending therefrom. Cylindrical connector 804a, 804b, etc encompasses one end of fiber 805a, 805b, etc, and is situated opposite cannular tip 802a, 802b, etc. in the housing 801a, 801b, etc. It is surrounded by a space 806a, 806b, etc. to allow for connection to the handpiece. The cylindrical connector 804a, 804b, etc. also defines an axis. Each cannular tip 802a, 802b, etc, contains a channel 803a, 803b, etc. and is bent (as is the contained channel 803a, 803b, etc.) to an angle relative to the axis. Fiber 805a, 805b, etc. extends from cylindrical connector 804a, 804b, etc., through channel 803a, 803b, etc. and has its distal end extend out cannular tip 802a, 802b, etc., following the bend in the tip, thereby redirecting the laser received from the connected handpiece.

Although the present invention has been described with reference to preferred embodiments, numerous modifications and variations can be made and still the result will come within the scope of the invention. No limitation with respect to the specific embodiments disclosed herein is intended or should be inferred.

What is claimed is:

1. A laser transmission system, comprising:
a portable console;
a laser generation module housed within the portable console;
control electronics housed within the portable console and electrically coupled to the laser generation module;
a touch screen having a graphical user interface through which user input is communicated to the control electronics;
a laser transmission fiber having a first end and a second end, the first end in laser communication with the laser generation module;
a laser application tip removably coupled to the second end of the laser transmission fiber;
connection structure to couple the laser application tip and laser transmission fiber; and
a wireless remote control foot switch that controls at least one function of the laser transmission system.

2. The laser transmission system of claim 1, further comprising a docking station for the console.

3. The laser transmission system of claim 2, wherein the portable console further comprises a battery pack.

4. The laser transmission system of claim 3, wherein the docking station serves to recharge the battery pack of the console.

5. The laser transmission system of claim 4, the laser generation module capable of simultaneously emitting multiple wavelengths of laser light in a single beam.

6. The laser transmission system in claim 1, the laser generation module further comprising:

a plurality of laser generation chips, each capable of emitting a laser beam having a wavelength unique from other laser generation chips in the plurality, each laser generation chip also being attached to a heat sink;

a plurality of monitor chips, each being placed on said heat sink behind the laser chip so as to monitor the laser output from each laser generation chip;

at least one collimating lens for each laser generation chip;

at least one filter/reflector structure, each in the path of at least two lasers, each said filter/reflector structure being transparent to at least one laser beam and reflective to at least one laser beam so as to turn any laser beam to which the filter/reflector structure is reflective into a path of a laser beam for which the filter/reflector structure is transparent;

an exit fiber into which all laser beams are conducted for further transportation; and control components and circuitry to power and control the laser chips from the console.

7. The laser module of claim 6, the number of laser generation chips being at least three.

8. The laser module of claim 7, the laser generation chips being in an orthogonal relationship to one another and the at least one filter/reflector structure.

\* \* \* \* \*